(12) United States Patent
Kurata et al.

(10) Patent No.: US 6,653,521 B1
(45) Date of Patent: Nov. 25, 2003

(54) ABSORBENT ARTICLE

(75) Inventors: Yuri Kurata, Kagawa (JP); Nobuhiro Kurata, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 95 days.

(21) Appl. No.: 09/675,881

(22) Filed: Sep. 29, 2000

(30) Foreign Application Priority Data

Oct. 4, 1999 (JP) .......................................... 11-282493

(51) Int. Cl.[7] .................................................. A61F 13/15
(52) U.S. Cl. ....................................................... 604/359
(58) Field of Search ................................ 604/359, 258, 604/385.01

(56) References Cited

U.S. PATENT DOCUMENTS

| | | | | |
|---|---|---|---|---|
| 4,186,743 A | * | 2/1980 | Steiger | 428/905 |
| 5,591,146 A | | 1/1997 | Hasse | 604/359 |
| 5,769,833 A | * | 6/1998 | Hasse | 604/359 |
| 5,951,534 A | | 9/1999 | Cummings et al. | 604/359 |
| 6,245,693 B1 | * | 6/2001 | Gagliardi et al. | 442/76 |
| 6,468,517 B2 | * | 10/2002 | Moscherosch | 424/76.1 |

FOREIGN PATENT DOCUMENTS

| | | |
|---|---|---|
| DE | 19603840 A1 | 8/1997 |
| JP | 05-068694 | 3/1993 |
| WO | WO 96/06589 | 3/1996 |

* cited by examiner

Primary Examiner—Weilun Lo
Assistant Examiner—C. Lynne Anderson
(74) Attorney, Agent, or Firm—Darby & Darby

(57) ABSTRACT

Provided is an absorbent article including a liquid-permeable top sheet facing the liquid-receiving side, a hydrophobic sheet and a liquid-absorbing layer located between the top sheet and the hydrophobic sheet. Furthermore, a deodorant is disposed on the outer side of the hydrophobic sheet.

7 Claims, 3 Drawing Sheets

ABSORBENT ARTICLE

BACKGROUND OF THE INVENTION

1. Field of the Invention

The present invention relates to an absorbent article for sanitary napkins, pantiliners, incontinence pads and the like. More particularly, it relates to an absorbent article having a deodorization function.

2. Description of the Related Art

A main object of an absorbent article including the sanitary napkins, the pantiliners, the incontinence pads and the like is to absorb the excrements discharged from the body such as menstrual blood, urine and sweat, and to retain the excrements in the absorbent article without flowback.

When the absorbent article which absorbed the excrements is kept on for a long time, microorganisms such as a bacteria which are normally present between crotches or the like propagate itself using the excrements as a propagation bed whereby unpleasant odors are apt to be generated.

Prior arts for deodorization of such unpleasant odors are disclosed in Japanese Unexamined Patent Publication (Kokai) No. Heisei 5-68694 and International Unexamined Patent Publication (Kohyo) No. Heisei 10-508218, for example.

Japanese Unexamined Patent Publication (Kokai) No. Heisei 5-68694 discloses an absorbent article in which an absorbent is arranged between a liquid-permeable top material and a liquid-impermeable back material, and an absorbent paper to which antibacterial silica gel and acrylic resin are applied or impregnated is arranged on a top surface or a back surface of the absorbent. By using the antibacterial silica gel and the acrylic resin as antibacterial agents, growth of the microorganisms owing to the excrements absorbed by the absorbent article is suppressed, and generation of the unpleasant odors due to the growth of microorganisms is prevented. In conjunction therewith, the odors of the excrements are deodorized due to a deodorization function of the antibacterial agent.

The absorbent article disclosed in International Unexamined Patent Publication (Kohyo) No. Heisei 10-508218 has substantially the same constitution as in Japanese Unexamined Patent Publication (Kokai) No. Heisei 5-68694. Namely, a bentonite clay is incorporated into an absorption core as a deodorant.

In addition, there is a deodorization method in which a fragrance is applied to the absorbent article for deodorization of the unpleasant odors. With regard to applying the fragrance, there are some methods, for example, a method of directly spraying the fragrance on the absorbent article, a method of sprinkling a solid and powdery aromatizer along with an absorbent polymer, and the like.

However, in the absorbent articles disclosed in Japanese Unexamined Patent Publication (Kokai) No. Heisei 5-68694 and International Unexamined Patent Publication (Kohyo) No. Heisei 10-508218, the deodorant such as silica gel or bentonite clay is directly immersed in excrements when the excrements are absorbed. Therefore, the surface of the porous deodorant is covered by the excrements whereby there is a problem that the deodorization function is not fully achieved or, in other words, the deodorization effect is to be decreased.

Further, in the method of applying the fragrance set forth above, there is a problem whether the fragrance suits one's taste or not. In addition, there may be strong fragrance which cannot be fully masked. Furthermore, in the method of directly spraying the fragrance on the absorbent article, the fragrance is diffused around the manufacturing machine during manufacturing process and the fragrance adheres to other extraneous products whereby there is a problem that the room must be partitioned for preventing the diffusion of fragrance.

In addition, in the case of utilizing the solid powdery aromatizer, the cost for processing is high, thereby increasing the product cost thereof.

SUMMARY OF THE INVENTION

An object of the invention is to provide an absorbent article adapted for preventing a deodorization function of the absorbent article from being degraded to fully achieve the deodorization effect.

According to an aspect of the invention, an absorbent article of the invention may comprise a liquid-permeable top sheet facing the liquid-receiving side, a hydrophobic sheet and a liquid-absorbing layer located between the top sheet and the hydrophobic sheet, wherein a deodorant is disposed on the outer surface of the hydrophobic sheet.

Preferably, a sticky layer for preventing slippage is arranged on the outer side of the hydrophobic sheet, and the deodorant is disposed between the hydrophobic sheet and the sticky layer.

Also preferably, a back sheet is arranged on the outer side of the hydrophobic sheet and, the deodorant is disposed between the hydrophobic sheet and the back sheet.

An adhesive layer may be applied to the outer side of the hydrophobic sheet to fix the deodorant on the outer surface of the hydrophobic sheet.

In the absorbent article of the invention, the deodorant is disposed on the outer side of the hydrophobic sheet which is located at the back side of the liquid-absorbing layer. Therefore, when the excrements are provided with the liquid-absorbing layer, it is possible to prevent the deodorant from being directly immersed in the excrements. Accordingly, permeation of the excrement liquid into many pores formed on the surface and inside of the deodorant can be prevented whereby the inherent deodorization function of the deodorant are not degraded.

It is preferred that the deodorant is granular or powdery, and is at least one selected from activated carbon, zeolite, silica gel and bentonite.

In other words, the deodorant may be any one of an adsorption type agent such as activated carbon, zeolite, silica gel and bentonite or may be a combination of the agent such as activated carbon and zeolite, or activated carbon, zeolite and silica gel.

It is further preferred that the gas permeability of the second sheet is less than 300 (cm$^3$/cm$^2$·s) by a method A using a fragile type testing machine as stipulated in JIS L-1096.

Accordingly, the unpleasant odors generated from the excrements can be effectively adsorbed and the leakage of the liquid can be prevented as well.

DESCRIPTION OF THE PREFERRED EMBODIMENT

The invention will be described hereinafter with reference to the accompanying drawings.

Figure 1:
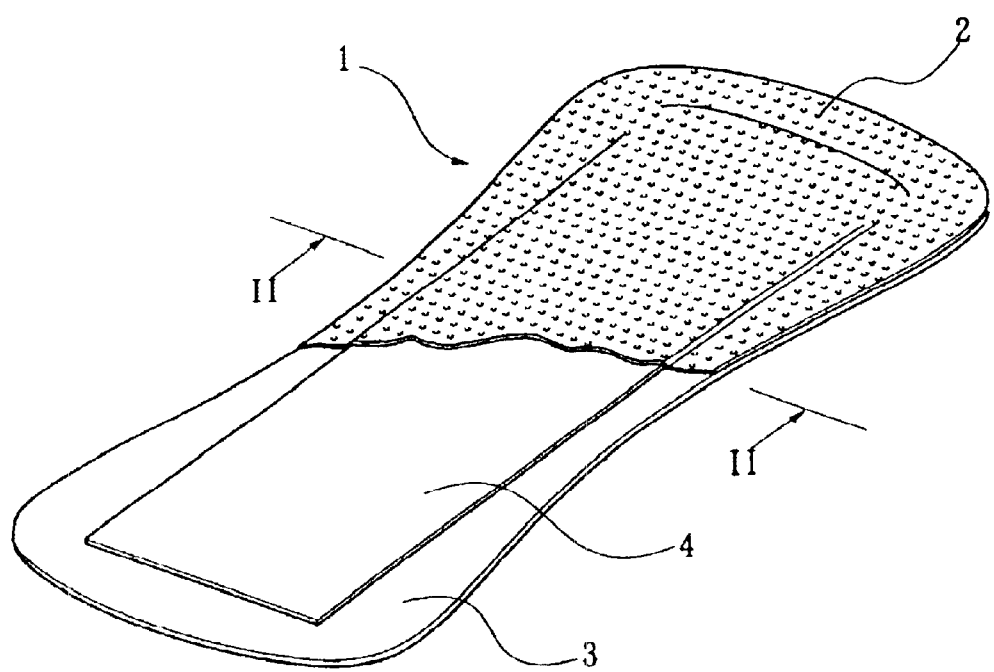
FIG. 1 is a perspective view of a partially cutaway sanitary napkin according to one embodiment of the invention.
Figure 2A:
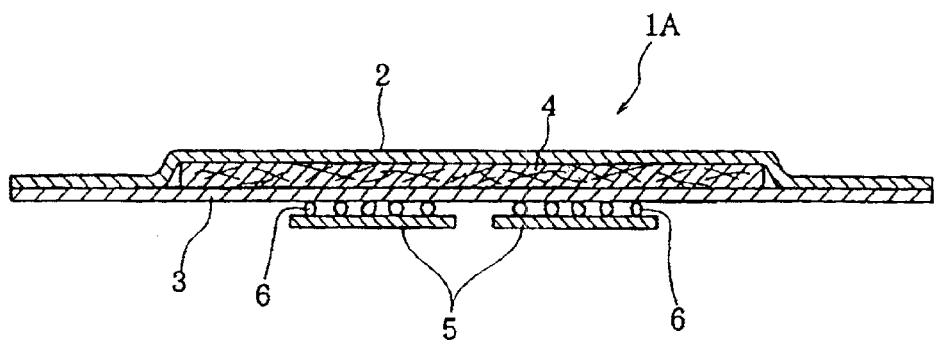
FIG. 2A is a cross section taken along the line II—II of FIG. 1.

FIG. 1 is a perspective view of a partially cutaway sanitary napkin according to one embodiment of the invention. FIG. 2A is a cross section taken along the line II—II of FIG. 1, and FIG. 2B and FIG. 2C are cross sections showing other embodiments.

As shown in FIG. 1, a sanitary napkin 1 basically has a three-layered structure composed of a liquid-permeable top sheet 2 which is a liquid-receiving side directly contacting the skin, an impermeable hydrophobic sheet 3 and an absorption sheet (liquid-absorbing layer) 4 which is arranged between the top sheet 2 and the hydrophobic sheet 3.

In the sanitary napkin 1A of the first embodiment shown in FIG. 2A, a sticky layer 5 for preventing slippage relative to the underwear is arranged on the outer surface of the hydrophobic sheet 3. The hydrophobic sheet 3 is adapted for completely or substantially completely stop the leakage of the liquid toward the outer surface side. Furthermore, a deodorant 6 is disposed between the hydrophobic sheet 3 and the sticky layer 5. When a colored one is used as the sticky layer 5, the deodorant 6 cannot be visually observed through the sticky layer 5.

Figure 2B:
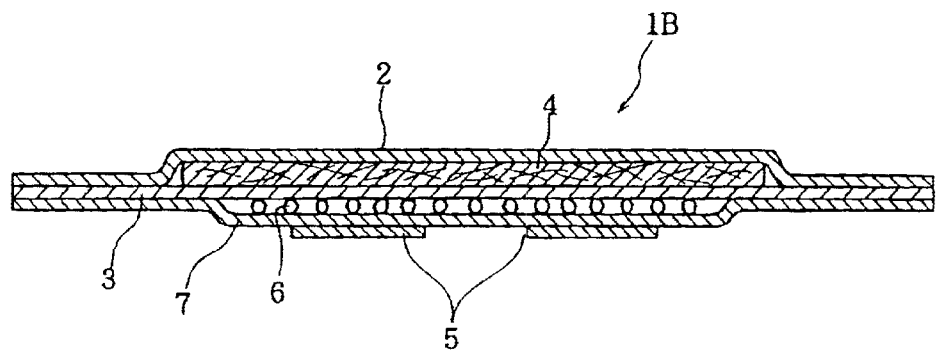
FIG. 2B is a cross section of the sanitary napkin according to the second embodiment of the invention.
Figure 2C:
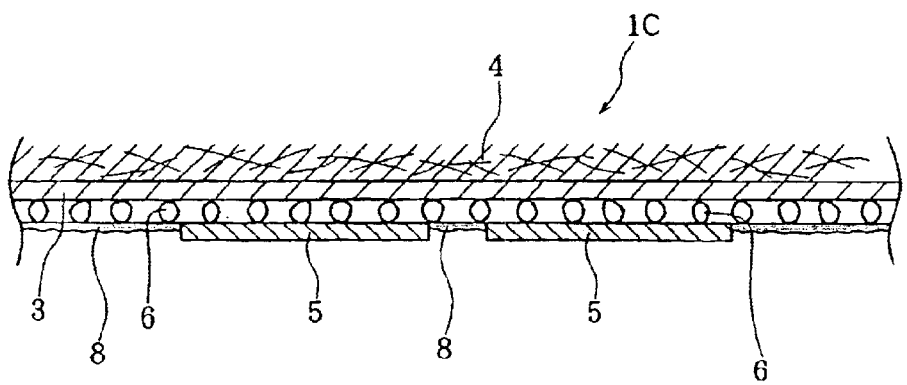
FIG. 2C is an enlarged cross section of the back surface side of the sanitary napkin according to the third embodiment of the invention.

In the sanitary napkin 1B of the second embodiment shown in FIG. 2B, a back sheet 7 is arranged on the outer side of the hydrophobic sheet 3 and, a deodorant 6 is disposed between the hydrophobic sheet 3 and the back sheet 7. In case where the hydrophobic sheet 3 is adapted to completely or substantially completely stop the liquid leakage, it is not always necessary that the back sheet 7 is liquid-impermeable. On the other hand, the hydrophobic sheet 3 may permit some liquid leakage, and the back sheet 7 may completely or substantially completely stop the liquid leakage. In other words, it is acceptable in case where the liquid impermeability of the back sheet 7 is higher than that of the hydrophobic sheet 3.

In addition, the sticky layer 5 for preventing slippage which is fixed to the underwear is provided on the outer surface of the back sheet 7. In this sanitary napkin 1B, the back surface side has a double structure composed of the hydrophobic sheet 3 and the back sheet 7. Accordingly, it is possible to improve the effect of preventing the liquid leakage as compared with the above sanitary napkin 1A. Further, since the deodorant 6 is covered by the back sheet 7, the deodorant 6 is not visually observed from the back surface side.

FIG. 2C is an enlarged cross section of the back surface side of the sanitary napkin 1C of the third embodiment. In this embodiment, an adhesive layer 8 is applied on the outer surface of the hydrophobic sheet 3 to fix the deodorant 6 on the outer surface of the hydrophobic sheet 3. It should be noted that the hydrophobic sheet 3 is adapted to completely or substantially completely stop the liquid leakage toward the outer surface side. The adhesive layer 8 is an anaerobic adhesive or a heat-hardening adhesive, and exhibits almost no adhesion in a hardened state. Further, on the portion in which the adhesive layer 8 is not applied, the sticky layer 5 for preventing slippage similar to that shown in FIG. 2A is arranged and, the deodorant 6 is also disposed between the sticky layer 5 and the hydrophobic sheet 3.

In the embodiment shown in FIG. 2C, it is possible that the deodorant 6 is widely distributed even in an area where no sticky layer 5 for preventing slippage is not arranged, so that the deodorization effect can be improved.

The liquid-permeable top sheet 2 may be a liquid-permeable material, that is, a material which permeates the liquid excrements such as menstrual blood, urine and sweat, for example. The top sheet may include, for example, a spun-lace nonwoven fabric, a point-bond nonwoven fabric, a spun-bond nonwoven fabric or a woven fabric, respectively constituted by hydrophilic fibers and/or hydrophobic fibers. The hydrophobic sheet 3 may be a spun-lace nonwoven fabric, a point-bond nonwoven fabric, a spun-bond nonwoven fabric or a woven fabric, respectively constituted by hydrophobic fibers and subjected to a water-repelling treatment. The absorption sheet (liquid-absorbing layer) 4 may be formed, for example, of pulp, tissue or hydrophilic nonwoven fabric and may contain a super absorbent polymer (SAP) or the like. The sticky layer 5 may be a material adapted to achieve an adhesive effect on both sides thereof, for example, a hot-melt type adhesive for fixation and a double-faced adhesive tape and the like. There is no particular limitation therefor. The back sheet 7 may be a polyolefin resin sheet or the like, for example. On the other hand, a nonwoven fabric may be used as the back sheet 7 and a water-proof film may be arranged between the back sheet 7 and the absorption sheet 4.

With regard to the hydrophobic sheet 3, its gas permeability was measured by a method A using a fragile type testing machine as stipulated in JIS L-1096.

Figure 3:
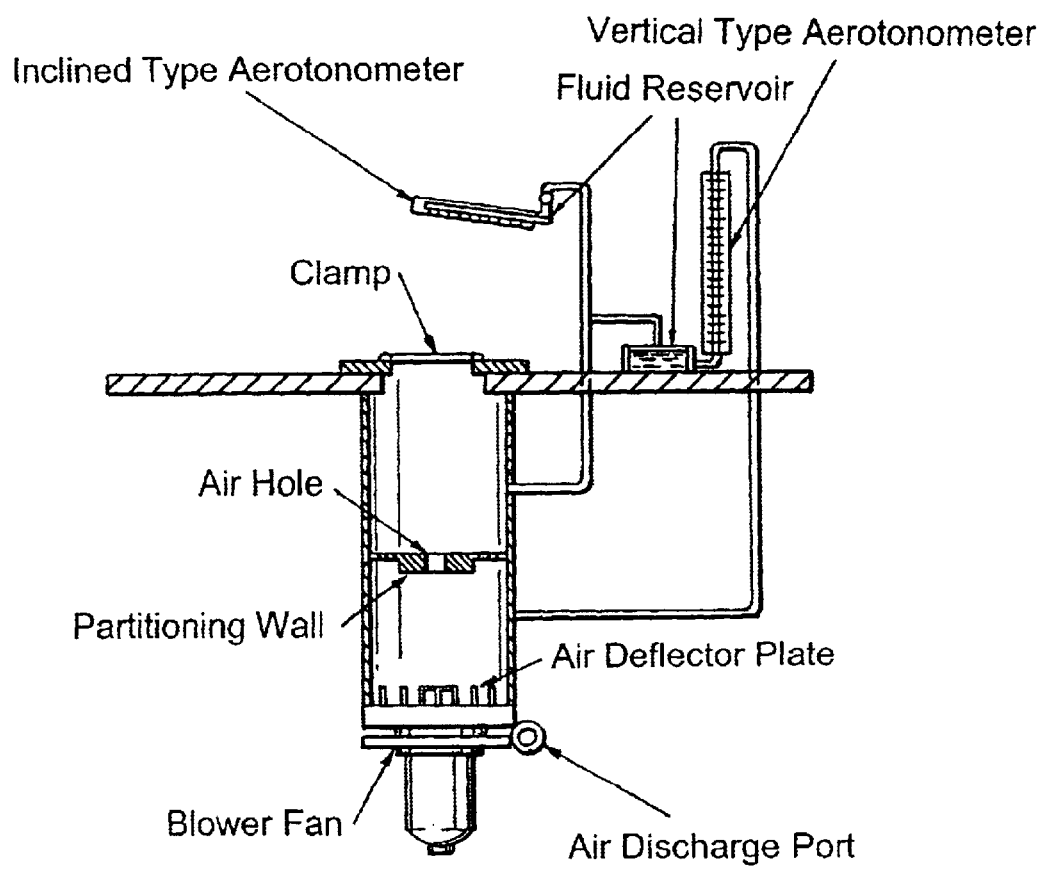
FIG. 3 is a illustration of a fragile type tester as stipulated in the JIS L-1096 standard.

6.27: Gas Permeability 6.27.1 A Method:

In accordance with the JIS L-1096 standard, after mounting a test piece of an appropriate size on one end of a cylinder, using a fragile type tester such as shown in FIG. 3, a variable resistor withdraws water such that an inclined aerotonometer indicates a pressure of 1.27 cm of water column. By adjusting a suction fan, the amount of air $cm^3/cm^2 \cdot s$ passing through the test piece is derived from a table attached to the tester on the basis of the pressure indicated by a vertical type aerotonometer and the kind of air hole to be used. Five measurements are performed, and an average value is used to indicate the gas permeability ( to an accuracy of one place decimal).

As a result, in case where the gas permeability was less than 0.1 $(cm^3/cm^2 \cdot s)$, it was confirmed that the amount of unpleasant odors permeating through the hydrophobic sheet 3 was decreased whereby the deodorization function was degraded. On the other hand, in case where the gas permeability was in a range of 300 $(cm^3/cm^2 \cdot s)$ or more, it was confirmed that leakage of the liquid took place.

From this measured result, the range of the gas permeability of the hydrophobic sheet 3 by the method A using a fragile type testing machine as stipulated in JIS L-1096 is less than 300 $(cm^3/cm^2 \cdot s)$. More preferred range is from 10 $(cm^3/cm^2 \cdot s)$ to 300 $(cm^3/cm^2 \cdot s)$.

The deodorant 6 is a porous adsorption type deodorant. For example, it may be well-known granular or powdery agent such as activated carbon, zeolite, silica gel and bentonite. The activated carbon may be an impregnated activated carbon such as that impregnated with alkali or acid.

Zeolite is expressed as $x/nM \cdot nAlO_2 \cdot ySiO_2 \cdot zH_2O$ wherein x and y each is an integer, M is a cation and n is a charge of the cation. M covers a wide range of cation such as $Na^+$, $K^+$, $NH^{4+}$, alkylammonium and heavy metal. Bentonite is a natural mineral and includes calcium bentonite and sodium bentonite.

In the sanitary napkin 1 shown in FIG. 1 and FIGS. 2A to 2C, the deodorant 6 is disposed on the outer side of the hydrophobic sheet 3, but not disposed between the top sheet 2 and the hydrophobic sheet 3, particularly in the absorption sheet 4 for absorbing the excrements. Accordingly, it is possible to prevent the deodorant 6 from being immersed in the excrements, so that many pores on the surface of the deodorant 6 cannot be clogged by permeation of the excrement liquid. Consequently, even after the sanitary napkin 1 absorbs the excrements, it is still possible to fully achieve the deodorization function of the deodorant 6. In other words, it is possible to prevent the deodorization function from being degraded, thereby permitting absorbing the unpleasant odors for a long period.

EXAMPLES

Tests for the deodorization effect were carried out for the shown embodiments of the absorbent articles.

The following tests (I), (II) and (III) are tests for deodorization effect to an alkaline malodorous substance, and the test procedure and the sample material are as follows.

(Test Procedure)

(1) 70 ppm of Ammonia was filled in an Erlenmeyer flask.

(2) The top sheet 2 side of a test sample piece (diameter: 50 mm) was fixed so as to directly contact the ammonia in the Erlenmeyer flask. In order to prevent the odors from permeating through the sample piece and leaking out of the Erlenmeyer flask, a polyvinylidene film was used for a tight sealing.

(3) After a predetermined time, concentration of ammonia in the Erlenmeyer flask was measured using a detector tube.

(4) Residual ratio of ammonia in the Erlenmeyer flask was derived from the following formula.

Residual Ratio (%)=(ammonia concentration in the Erlenmeyer flask after the predetermined time)/(ammonia concentration in the Erlenmeyer flask in initial stage)×100

(Sample Material)

Example 1

The sanitary napkin 1A having a cross-sectional structure as shown in FIG. 2A was taken as Example 1. Its specification was as follows. (1) The liquid-permeable top sheet 2 was a cotton-spun lace having the weight of 30 g/m²; (2) The hydrophobic sheet 3 was prepared by a water-repelling treatment of a spun-bond nonwoven fabric formed from a compound fiber of PET/PP. The weight thereof was 45 g/m²; (3) The absorption sheet 4 was composed of an air-laid pulp having the weight of 45 g/m² and an air-laid nonwoven fabric having the weight of 40 g/m²; (4) The sticky layer 5 was applied with a hot-melt type adhesive so that the applied area ratio to the hydrophobic sheet 3 was 50%; and (5) The deodorant 6 was Kuraraycoal (manufactured by Kuraray Chemical Co., Ltd.) having a standard grain size of 14 to 32 meshes. Furthermore, the weight of the deodorant 6 was 25 g/m² in the range of the area where the sticky layer 5 for preventing slippage was arranged.

Example 2

This had the same structure as in Example 1 except that the weight of the deodorant 6 was 50 g/m² in the range of the area where the sticky layer 5 for preventing slippage was arranged.

Comparative Example 1

Instead of disposing the deodorant 6 between the hydrophobic sheet 3 and the sticky layer 5 in the sanitary napkin 1A, the deodorant 6 was incorporated into the absorption sheet 4 to such an extent that the total amount was same as in Example 1.

Comparative Example 2

Instead of disposing the deodorant 6 between the hydrophobic sheet 3 and the sticky layer 5 in the sanitary napkin 1A, the deodorant 6 was incorporated into the absorption sheet 4 to such an extent that the total amount was same as in Example 2.

Comparative Example 3

This was similar to the sanitary napkin 1A except for eliminating the deodorant 6.

(Test Conditions)

(I) Deodorant Test in Dry State

Test was carried out in such a state that each of the foregoing Examples and Comparative Examples was dry.

(II) Deodorant Test in Wet State

In order to assume the state where the excrements were absorbed by the sanitary napkin, test was carried out in such a state that 0.05 g/p of glycerol was dropped onto the top sheet 2 of each of the foregoing Examples and Comparative Examples.

(III) Deodorant Test for Variation per Hour

In order to confirm the deodorization effect of the deodorant which was fixedly adhered by a hot-melt type adhesive upon variation per hour, the sample of Example 1 was allowed to stand in an oven of 40° C. for one week.

(Test Result)

(I) Result of the deodorant test in dry state is given in Table 1.

TABLE 1

| | Amount of the Deodorant Added (g/m²) | Residual Ratio of Ammonia (%) | | |
|---|---|---|---|---|
| | | Upon Initiation of the Test | After 1 Hour | After 4 Hours |
| Example 1 | 25 | 100 | 36 | 13 |
| Comp. Ex. 1 | 25 | 100 | 35 | 14 |
| Comp. Ex. 3 | 0 | 100 | 50 | 38 |
| Example 2 | 50 | 100 | 32 | |
| Comp. Ex. 2 | 50 | 100 | 31 | |
| Comp. Ex. 3 | 0 | 100 | 50 | |

As shown in Table 1, in case where the amount of the deodorant to be added was 25 g/m², the residual ratio after 1 hour was only one-half reduction (50%) in Comparative Example 3, while in Example 1 and Comparative Example 2, the residual ratio was 36% and 35%, respectively. The residual ratio after 4 hours was 38% in Comparative Example 3, while in Example 1 and Comparative Example 1, the residual ratio was 13% and 14%, respectively.

In case where the amount of the deodorant to be added was 50 g/m², the residual ratio after 1 hour was 50% in Comparative Example 3, while in Example 2 and Comparative Example 2, the residual ratio was 32% and 31%, respectively.

It was confirmed from the above table that the deodorization effect in dry state in case of Examples 1 and 2 where the deodorant 6 was disposed on the outer side of the hydrophobic sheet 3 as shown in FIG. 2A was equivalent to that in the case where the same amount of the deodorant 6 was incorporated into the absorption sheet 4. In other words, it is understood that the difference in the position of disposing the deodorant 6 does not cause a difference in the deodorization effect.

(II) Result of the deodorant test in wet state is given in Table 2.

TABLE 2

| | Amount of the Deodorant Added (g/m²) | Residual Ratio of Ammonia (%) | | |
|---|---|---|---|---|
| | | Upon Initiation of the Test | After 1 Hour | After 4 Hours |
| Example 1 | 25 | 100 | 36 | 10 |
| Comp. Ex. 1 | 25 | 100 | 41 | 17 |
| Comp. Ex. 3 | 0 | 100 | 49 | 40 |
| Example 2 | 50 | 100 | 33 | |
| Comp. Ex. 2 | 50 | 100 | 40 | |
| Comp. Ex. 3 | 0 | 100 | 48 | |

From the result shown in Table 2, it is understood that, in wet state, the deodorization effect is high in Example 1 where 25 g/m² of the deodorant was added as well as in Example 2 where 50 g/m² of the deodorant was added, in comparison with Comparative Example 1 and Comparative Example 2. It is also understood that the difference in the effect is significant especially when the elapsed time is longer (see the data after 4 hours).

Accordingly, it can be thought that, in Comparative Examples 1 and 2 where the deodorant 6 was incorporated into the absorption sheet 4, the deodorant 6 was directly immersed in glycerin used as a substitute for excrements whereby the porous surface of the deodorant 6 was covered by glycerin and results in a state where the inherent deodorization function cannot be fully achieved.

On the contrary, in Examples 1 and 2 where the deodorant 6 was disposed between the hydrophobic sheet 3 and the sticky layer 5, it is understood that a direct covering of the porous surface of the deodorant 6 by glycerol can be prevented to fully achieve the inherent deodorization function, resulting in a high deodorization effect as compared with Comparative Example 1 and Comparative Example 2.

(III) Result of the deodorant test for variation per hour is given in Table 3.

TABLE 3

| | Amount of the Deodorant Added (g/m²) | Residual Ratio of Ammonia (%) | | |
|---|---|---|---|---|
| | | Upon Initiation of the Test | After 1 Hour | After 4 Hours |
| Example 1 | 25 | 100 | 12 | 6 |

As shown in Table 3, in Example 1, the residual ratio of ammonia after 1 hour was 12% and that after 4 hours was 6%. From the result set forth above, it is understood that there is almost no influence of the hot-melt type adhesive on the deodorization effect upon variation per hour.

In the foregoing Examples, the sanitary napkin was exemplified as an absorbent article. However, the invention is not limited thereto but is applicable, for example, to the pantiliners, the incontinence pads, the disposable diapers and the like.

According to the invention, the deodorant is not directly immersed in the excrements, so that is possible to prevent the deodorization function of the absorbent article from being degraded, even after absorbing the excrements.

While the invention has been described in detail and with reference to specific embodiments thereof, it will be apparent to one skilled in the art that various changes and modifications can be made therein without departing from the sprit and scope thereof.

Here, 'comprises/comprising' when used in this specification is taken to specify the presence of stated features, integers, steps or components but does not preclude the presence or addition of one or more other features, integers, steps, components or groups thereof.

What is claimed is:

1. An absorbent article comprising:
   a liquid-permeable top sheet facing a liquid-receiving side,
   a hydrophobic sheet,
   a liquid-absorbing layer located between the liquid-permeable top sheet and the hydrophobic sheet,
   a colored sticky layer arranged on an outer side of the hydrophobic sheet for preventing slippage,
   a back sheet disposed between the hydrophobic sheet and the colored sticky layer, and
   a porous granular or powdered deodorant retained on an outer surface of the hydrophobic sheet for retention between the hydrophobic sheet and the back sheet in a non-releasable manner such that the deodorant functions for a long period of time.

2. An absorbent article comprising:
   a liquid-permeable top sheet facing a liquid-receiving side,
   a hydrophobic sheet,
   a liquid-absorbing layer located between the liquid-permeable top sheet and the hydrophobic sheet,
   a colored sticky layer arranged on an outer side of the hydrophobic sheet for preventing slippage,
   an adhesive layer applied on the outer side of the hydrophobic sheet, and
   a porous granular or powdered deodorant retained on an outer surface of the hydrophobic sheet for retaining the deodorant on the outer surface of the hydrophobic sheet with the sticky layer and the adhesive layer in a non-releasable manner such that the deodorant functions for a long period of time.

3. An absorbent article comprising:
   a liquid-permeable top sheet facing a liquid-receiving side,
   a hydrophobic sheet,
   a liquid-absorbing layer located between the liquid-permeable top sheet and the hydrophobic sheet, and
   a back sheet arranged on an outer side of the hydrophobic sheet,
   wherein a deodorant is retained on an outer surface of the hydrophobic sheet such that said deodorant is permanently retained between the hydrophobic sheet and the back sheet in a non-releasable manner such that the deodorant functions for a long period of time.

4. The absorbent article as set forth in claim 2 or 3, wherein the hydrophobic sheet is gas-permeable.

5. The absorbent article as set forth in claim 2, wherein the adhesive layer is at least one of an anaerobic adhesive and a thermosetting adhesive.

6. The absorbent article as set forth in claim 2 or 3, wherein the deodorant is granular or powdery, and is at least one selected from activated carbon, zeolite, silica gel and bentonite.

7. The absorbent article as set forth in claim 4, wherein the gas permeability of the hydrophobic sheet by a method A using a fragile type testing machine as stipulated in JIS L-1096 is less than 300 (cm³/cm²·s).

* * * * *